United States Patent
Mouloungui et al.

(10) Patent No.: US 9,765,011 B2
(45) Date of Patent: Sep. 19, 2017

(54) METHOD FOR SYNTHESISING DIMETHYL CARBONATE

(71) Applicants: CHARABOT SA, Grasse (FR); INSTITUT NATIONAL POLYTECHNIQUE DE TOULOUSE, Toulouse (FR); INSTITUT NATIONAL DE LA RECHERCHE AGRONOMIQUE, Paris (FR)

(72) Inventors: Zephirin Mouloungui, Toulouse (FR); Christophe Maruejouls, Cugnaux (FR); Sophie Lavoine-Hanneguelle, Mouans-Sartoux (FR)

(73) Assignees: CHARABOT SA, Grasse (FR); INSITUT NATIONAL POLYTECHNIQUE DE TOULOUSE, Toulouse (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 15/113,181

(22) PCT Filed: Jan. 19, 2015

(86) PCT No.: PCT/EP2015/050869
§ 371 (c)(1),
(2) Date: Jul. 21, 2016

(87) PCT Pub. No.: WO2015/110381
PCT Pub. Date: Jul. 30, 2015

(65) Prior Publication Data
US 2017/0001942 A1    Jan. 5, 2017

(30) Foreign Application Priority Data
Jan. 22, 2014  (FR) ...................... 14 50506

(51) Int. Cl.
| | | |
|---|---|---|
| *B01J 23/06* | (2006.01) | |
| *B01J 27/053* | (2006.01) | |
| *B01J 27/128* | (2006.01) | |
| *B01J 27/135* | (2006.01) | |
| *B01J 27/138* | (2006.01) | |
| *B01J 37/04* | (2006.01) | |
| *C07C 68/00* | (2006.01) | |
| *B01J 35/00* | (2006.01) | |
| *B01J 37/08* | (2006.01) | |

(52) U.S. Cl.
CPC .............. *C07C 68/00* (2013.01); *B01J 23/06* (2013.01); *B01J 27/053* (2013.01); *B01J 27/128* (2013.01); *B01J 27/135* (2013.01); *B01J 27/138* (2013.01); *B01J 35/0006* (2013.01); *B01J 37/04* (2013.01); *B01J 37/08* (2013.01)

(58) Field of Classification Search
None
See application file for complete search history.

(56) References Cited

U.S. PATENT DOCUMENTS

2012/0130111 A1    5/2012 Koh et al.

OTHER PUBLICATIONS

Wu, X., et al., "Synthesis of dimethyl carbonate by urea alcoholysis over Zn/Al bi-functional catalysts", Applied Catalysis A: General, vol. 473, Jan. 7, 2014 (Jan. 7, 2014), pp. 13-20, XP028622691, ISSN: 0926-860X, DOI: 10.1016/J.APCATA.2013.12.034.
Wang, H., et al., "Highly selective synthesis of dimethyl carbonate from urea and methanol catalyzed by ionic liquids", Fuel Processing Technology, Elsevier BV, NL, vol. 90, No. 10, Oct. 1, 2009 (Oct. 1, 2009), pp. 1198-1201, XP026611631, ISSN: 0378-3820, [retrieved on Jun. 17, 2009], DOI: 10.1016/J.FUPROC.2009.05.020.
Lian, H., et al., "Processing of lignin in urea/zinc chloride deep-eutectic solvent and its use as filler in a phenol-formaldehyde resin", RSC Advances, Jan. 1, 2012 (Jan. 1, 2012), XP055178399, ISSN: 2046-2069, DOI: 10.1039/C4RA16734A, 8 pages.
Abbott, A., et al., "Eutectic-Based Ionic Liquids with Metal-Containing Anions and Cations", Chemistry—A European Journal, vol. 13, No. 22, Jul. 27, 2007 (Jul. 27, 2007), pp. 6495-6501, XP055178320, ISSN: 0947-6539, DOI: 10.1002/chem.200601738.
Sumarokova, T., et al., "SnCl2.2(NH2)2CO and SnCl2.2(NH2)2CS", Izvestia Akademii Nauk Kazahskoj SSR. Seri Himiceskaa, Nauka Kazssr, Alma-Ata, KZ, vol. 18, No. 6, Jan. 1, 1968 (Jan. 1, 1968), pp. 76-18, XP008172301, ISSN: 0002-3205.
International Search Report, dated Apr. 8, 2015, from corresponding PCT Application.

*Primary Examiner* — Samantha Shterengarts
(74) *Attorney, Agent, or Firm* — Young & Thompson

(57) ABSTRACT

A method for synthesizing dimethyl carbonate from methanol and urea, in which a saline ureic medium is used that includes at least one inorganic salt selected from the group made up of zinc (Zn) (II) chloride, tin (Sn) chlorides and iron (Fe) (III) chloride, characterized in that: methanol, in the presence of a catalytic composition, is placed in contact with the saline ureic medium that is at least partially liquid at a temperature referred to as synthesis temperature, which is higher than 140° C., such that reaction vapors are produced; the reaction vapors are condensed, and a condensate of the reaction vapors is collected, including dimethyl carbonate; the method is carried out at atmospheric pressure. A method for enriching and purifying dimethyl carbonate is also described.

19 Claims, 1 Drawing Sheet

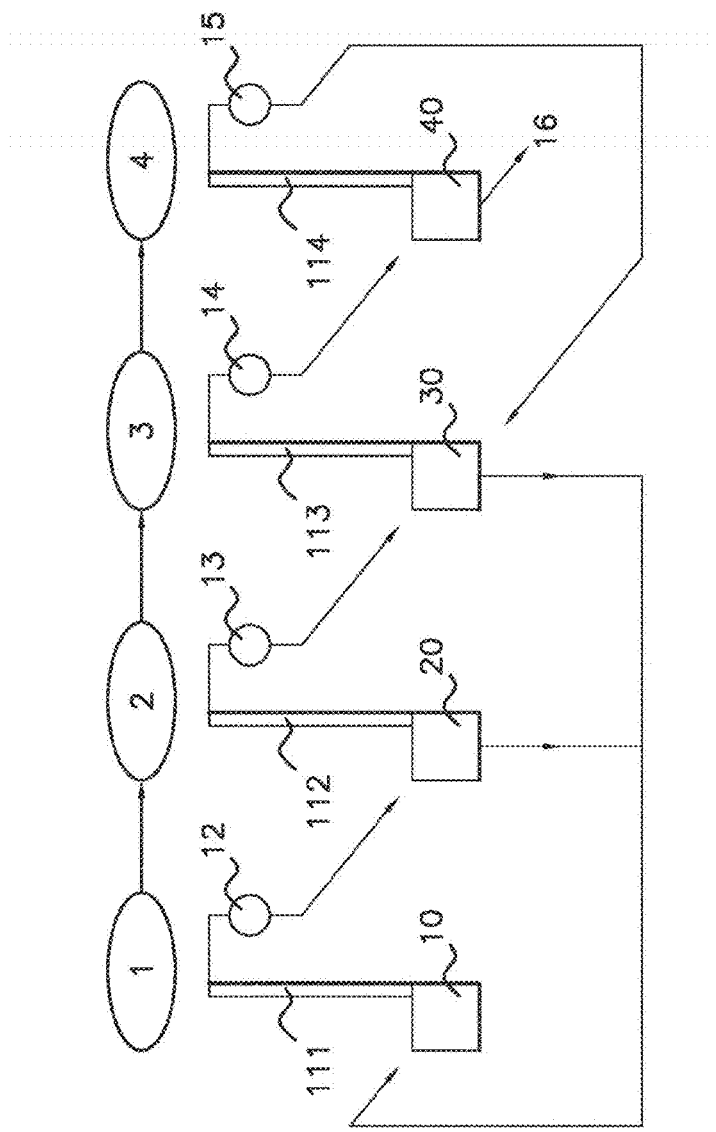

METHOD FOR SYNTHESISING DIMETHYL CARBONATE

The invention relates to a method for synthesizing dimethyl carbonate at atmospheric pressure starting from methanol and urea. The invention also relates to a method for enrichment of dimethyl carbonate by a composition that comprises dimethyl carbonate and methanol and a method for purifying dimethyl carbonate and for preparing dimethyl carbonate that is essentially pure and free of methanol.

Different methods making it possible to synthesize dimethyl carbonate are already known. A method for synthesizing dimethyl carbonate under pressure in an autoclave is known (Wu Xiaomin et al., (2014), Applied Catalysis A: General, 473, 13-20. Synthesis of Dimethyl Carbonate by Urea Alcoholysis over Zn/Al Bi-Functional Catalysts).

A method for synthesizing dimethyl carbonate at atmospheric pressure and at the temperature of 185° C. in which methanol in the gaseous state is introduced into a reactor that contains urea, ZnO as a catalyst, and 2-hydroxyethyl-N,N,N-trimethylammonium bis(trifluoromethylsulfonyl)imide (choline-NTf2) formed by a mixture of choline chloride (2-hydroxyethyl-N,N,N-trimethylammonium chloride) and lithium bis(trifluoromethylsulfonyl)imide is known from US 2012/0130111.

Such a method requires an element for preheating liquid methanol and its evaporation before its introduction in vapor form into the reactor. Such a method is therefore complex in its implementation. It also requires using 2-hydroxyethyl-N,N,N-trimethylammonium bis(trifluoromethylsulfonyl) imide that for its purification requires repeated steps of washing with water until chloride ions are completely eliminated. In addition, for its preparation, such a compound requires using the bis(trifluoromethylsulfonyl)imide lithium salt that is a toxic substance for the environment, in particular for aquatic organisms. Such a substance is in addition toxic for the user by ingestion and by contact with the skin.

The object of the invention is to remedy the above-mentioned drawbacks by proposing a method for synthesizing dimethyl carbonate that does not require the use of bis(trifluoromethylsulfonyl)imide lithium salt.

The object of the invention is also to propose a method for synthesizing dimethyl carbonate at atmospheric pressure starting from urea and methanol making it possible to obtain a high yield for conversion of the urea into dimethyl carbonate without using bis(trifluoromethylsulfonyl)imide lithium salt and that is therefore simplified. The object of the invention is also to propose a method for synthesizing dimethyl carbonate that is biosourced, i.e., that is obtained from natural and renewable resources such as methanol, ammonia, and carbon dioxide.

The object of the invention is also a composition that is obtained during the implementation of a method for synthesizing dimethyl carbonate according to the invention.

The object of the invention is also to reach these objectives at reduced cost, by proposing a method for synthesizing dimethyl carbonate of acceptable cost for its use on the industrial scale and not requiring specific means for controlling the pressure in the synthesis reactor.

The object of the invention is also more particularly to propose such a method for synthesizing dimethyl carbonate that is compatible with environmental protection constraints.

To do this, the invention relates to a method for synthesizing dimethyl carbonate starting from methanol and urea, in which a saline ureic medium comprising at least one inorganic salt selected from the group formed by zinc chloride (Zn) II, tin chlorides (Sn), and iron chloride (Fe) III is used:
characterized in that:
- Methanol, in the presence of a catalytic composition, is brought into contact with said saline ureic medium that is at least partially liquid at a temperature, so-called synthesis temperature, that is higher than 140° C., such that reaction vapors are produced;
- The reaction vapors are condensed, and a condensate of said reaction vapors and comprising dimethyl carbonate is recovered;
- The method is implemented at atmospheric pressure.

The invention therefore consists in proposing a method for catalytic synthesis of dimethyl carbonate at atmospheric pressure starting from urea and methanol according to the following diagram of reaction (I):

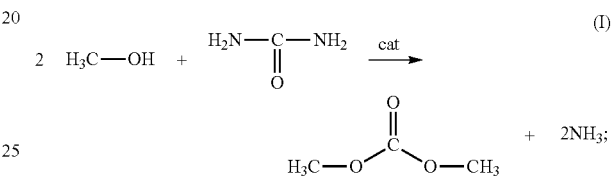

in which "cat" represents a catalyst.

Hereinafter:
- "Dimethyl carbonate" is the compound referenced in "Chemical Abstract Service" under the number CAS 616-38-6 and general formula (II) below:

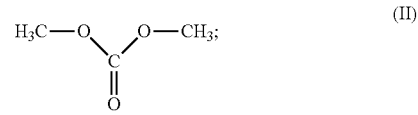

- The expression "inorganic salt" refers to an electrically neutral compound that is formed by at least one cation—in particular a cation of a metal element—and at least one anion, each of the cations and anions being inorganic by nature, i.e., essentially free of organic material based on carbon atoms or carbon atoms associated with other elements such as nitrogen (N), hydrogen (H), and oxygen (O);
- The expression "saline ureic medium" refers to a medium that comprises urea and at least one inorganic salt.

In a method according to the invention, (i) liquid methanol is reacted at atmospheric pressure with the urea of a saline ureic medium that is at least partially—in particular totally—liquid, comprising urea and at least one inorganic salt that is selected from the group that is formed by zinc chlorides (Zn), tin chlorides (Sn), and iron chloride (Fe) III (i.e., iron with a degree of oxidation that is equal to 3), in the presence of at least one catalyst at the synthesis temperature, with said synthesis temperature being adapted to allow the formation of reaction vapors from the reaction medium, (ii) these reaction vapors are condensed, and (iii) this condensate that comprises dimethyl carbonate is recovered.

In a method according to the invention, a saline ureic medium that is at least partially liquid and is formed starting from urea and at least one inorganic salt selected from the group that is formed by zinc chloride (Zn) II, tin chlorides (Sn)—in particular tin chloride (Sn) II—and iron chloride (Fe) III are formed by heating, and methanol is brought into contact with this saline ureic medium that is at least partially liquid. The saline ureic medium therefore has a liquid phase at the reaction temperature. It is possible, however, that it also has a solid phase.

The inventors determined that the use of such a saline ureic medium that comprises at least one such inorganic salt and urea is apt to retain at least a portion of the methanol in the saline ureic medium and to make possible its reaction with urea in the presence of the catalyst for forming dimethyl carbonate.

The inventors also noted that the saline ureic medium makes it possible to keep at least a portion of the methyl carbamate that is a synthesis intermediary means formed starting from urea and methanol and therefore makes possible its reaction with methanol to form dimethyl carbonate. The saline ureic medium therefore makes it possible to retain the synthesis intermediary and to limit—and even to prevent—its entrainment in vapor form. A condensate is thus formed that comprises dimethyl carbonate and that is essentially free of methyl carbamate. A final step for separation of the dimethyl carbonate and the methyl carbamate is therefore useless.

In a method according to the invention, a reaction medium is formed that comprises the saline ureic medium that can keep methanol at a temperature that is higher than 140° C. and the catalyst, methyl carbamate and dimethyl carbonate are formed, and the dimethyl carbonate formed outside of the reaction medium is extracted in such a way as to shift the equilibrium of the reaction in terms of the consumption of urea, methanol and methyl carbamate, and in terms of the formation of dimethyl carbonate.

In addition, the inventors noted that the saline ureic medium makes it possible to modulate the elimination/retention of ammonia in the gaseous state released during the reaction of methanol and urea (or methyl carbamate). Such elimination/retention makes it possible to modulate the kinetic parameters and the equilibrium of the reaction.

Thus, a method according to the invention makes it possible to keep the reagents (methanol, urea) and the synthesis intermediary (methyl carbamate) in the saline ureic medium at the synthesis temperature but also makes it possible to extract the product of the reaction (dimethyl carbonate) by condensation of the vapors of the reaction medium.

Advantageously and according to the invention, each salt of the saline ureic medium is selected from the group formed by $SnCl_2$, $FeCl_3$ and $ZnCl_2$ and their mixtures. Thus, the saline ureic medium is formed exclusively by at least one inorganic salt and urea.

Advantageously and according to the invention, the synthesis temperature is higher than approximately 140° C.

Advantageously and according to the invention, the synthesis temperature is between approximately 140° C. and approximately 160° C.

Advantageously and according to the invention, during a first operating step, a reaction medium that comprises the saline ureic medium, the catalytic composition and a first quantity of methanol is formed, and the reaction medium is kept at the synthesis temperature, with the formed condensate being reintroduced into the reaction medium, and then during a second subsequent operating step, a stream of methanol is introduced into the reaction medium, and a stream of the condensate of the vapors of the reaction medium is sampled. In a method according to the invention, the first operating step is carried out by reintroducing the condensate into the reaction medium, i.e., without sampling said condensate. During the second subsequent operating step, the condensate is sampled, and a stream of methanol in the reaction medium is introduced simultaneously into said sampling. Advantageously and according to the invention, the first operating step is carried out under conditions called "at an infinite reflux level," such that the ratio between the liquid volume that is condensed (reflux) and reintroduced into the reaction medium and the liquid volume that is condensed (condensate) and separated from the reaction medium is infinite, i.e., the entire condensate is reintroduced into the reaction medium.

Advantageously, all of the steps of the method according to the invention are carried out under atmospheric pressure.

Advantageously and according to the invention, the first operating step is carried out in a container at atmospheric pressure and the second operating step is carried out in the same container at atmospheric pressure.

Advantageously and according to the invention, the first operating step is of a duration of about 15 minutes. The reaction medium is therefore kept at an infinite reflux level for a duration of about 15 minutes.

Advantageously and according to a first variant of a method in accordance with the invention, methanol is added into the reaction medium in a continuous stream. According to this first variant, the stream of methanol added into the reaction medium is therefore a stream that is uninterrupted for the entire duration of the reaction. The possibility is not ruled out, however, of varying the value of this stream, with said stream value being greater than or equal to a non-zero minimal stream value.

Advantageously, methanol is added into the reaction medium in a continuous stream, and the condensate that comprises dimethyl carbonate is recovered continuously during the reaction. The flow rate of the methanol stream introduced into the reaction medium and the heating temperature are adapted in such a way as to form dimethyl carbonate by synthesis, to collect reaction vapors, and to recover the condensate that comprises dimethyl carbonate.

Advantageously and according to a second variant of a method according to the invention, methanol is added into the reaction medium in an intermittent stream. According to this second variant, successive additions of defined (discreet) quantities of methanol in the reaction medium are initiated. The frequency of addition and the volume of these predetermined quantities of methanol are adapted in such a way as to form dimethyl carbonate in the reaction medium, its evaporation and its condensation to form the condensate.

Advantageously, methanol is added into the reaction medium in an intermittent stream, and the condensate comprising dimethyl carbonate is recovered continuously during the reaction.

As a variant, methanol is added into the reaction medium in an intermittent stream, and the condensate that comprises dimethyl carbonate is recovered by successive samplings. The condensate that comprises dimethyl carbonate is therefore sampled intermittently. A number of successive discrete additions of methanol are therefore carried out in the reaction medium, and the condensate that comprises dimethyl carbonate is recovered by successive samplings.

Advantageously and according to the invention, the saline ureic medium is formed initially by heating a saline composition comprising each inorganic salt and urea. In a method according to the invention, a saline ureic medium is therefore formed in the at least partially liquid state by heating the saline composition.

The possibility of forming the saline ureic medium directly by heating a saline composition formed solely by each inorganic salt and urea is not ruled out, however. The saline ureic medium thus consists solely of each inorganic salt and urea.

Advantageously and according to the invention, the saline composition is heated to a temperature of between 80° C. and 125° C.—in particular approximately 100° C.—and for a duration of at least 10 minutes—in particular between 10 minutes and 3 hours. The saline composition is therefore heated to a sufficient temperature to form the saline ureic medium in the at least partially liquid state.

Advantageously, in a method according to the invention:
The saline ureic medium is first formed by heating each inorganic salt and urea to a temperature of between 80° C. and 125° C. for a duration of between 10 minutes and 3 hours, and then;
The catalytic composition is added to the formed saline ureic medium, and then;
During the first operating step, a first quantity of methanol is added, then the mixture that is obtained is brought to a temperature of higher than 140° C.—in particular between approximately 140° C. and approximately 160° C.—and this temperature is maintained for 15 minutes with neither supplementary addition of methanol nor collecting of condensate formed from reaction vapors, and then;
During the second operating step, a stream of methanol is added, and the reaction vapors are collected.

Advantageously and according to the invention, the saline ureic medium is prepared with an initial quantity of urea and an initial quantity of each inorganic salt in a ratio by mass of each inorganic salt in relation to the urea of between 2 and 10.

Advantageously and according to the invention, the saline ureic medium is prepared with an initial quantity of urea and an initial quantity of inorganic salts, with the inorganic salts and the urea being present in the ureic medium in a ratio by mass of inorganic salts in relation to the initial urea of between 4 and 10.

The possibility of producing the saline ureic medium by heating the mixture formed by each inorganic salt, urea, catalyst and a first quantity of methanol at the reaction temperature without sampling the condensate of the reaction vapors, and then of adding the methanol stream by sampling the condensate of the reaction vapors is not ruled out. As a variant, it is possible to prepare the saline ureic medium by heating urea and one or a number of inorganic salts and then by adding a quantity of the catalytic composition in the methanol.

Advantageously and according to the invention, the saline ureic medium is a conductive—in particular electro-conductive and thermo-conductive—medium.

Advantageously and according to the invention, the catalytic composition comprises at least one compound that is selected from the group that is formed by zinc oxide and zinc sulfate.

Advantageously, as a variant or in combination, the catalytic composition comprises a zinc oxide. Advantageously, as a variant or in combination, the catalytic composition is formed by zinc oxide. Advantageously and according to the invention, the catalytic composition also comprises zinc sulfate. Advantageously and according to the invention, the catalytic composition comprises zinc oxide and zinc sulfate—in particular in essentially equal proportions by mass.

Advantageously and according to the invention, the catalytic composition consists of (i.e., is formed solely by) zinc oxide and zinc sulfate—in particular in essentially equal proportions by mass.

Advantageously and according to the invention, the catalytic composition is in the solid state. Advantageously, it is therefore possible to recycle said solid catalytic composition for a subsequent use.

Advantageously and according to the invention, the catalytic composition is prepared by calcination of a solid mixture comprising zinc oxide and zinc sulfate at a temperature of between 300° C. and 700° C. Advantageously and according to the invention, the catalytic composition is prepared by calcination of a solid mixture formed solely by zinc oxide and zinc sulfate at a temperature of between 300° C. and 700° C.

Advantageously and according to the invention, methanol in the liquid state is added into the reaction medium. In a method for synthesis of dimethyl carbonate according to the invention, methanol in the liquid state is introduced into a reactor that is heated to the atmospheric pressure and that contains the saline ureic medium, reaction vapors comprising dimethyl carbonate are formed, and the condensate of said reaction vapors is recovered.

Advantageously, in a particular embodiment according to the invention, a stream of at least one portion—in particular the entirety—of the condensate of reaction vapors is introduced into a reaction medium kept at the synthesis temperature and comprising a quantity of saline ureic medium and a quantity of catalytic composition, such that reaction vapors are produced, said reaction vapors are condensed, and a condensate of said reaction vapors comprising dimethyl carbonate is recovered. Advantageously, in this embodiment of the invention, a step for recycling at least one portion—in particular the entirety—of the condensate of reaction vapors comprising methanol and dimethyl carbonate is carried out.

Advantageously and according to the invention, at least a portion of the condensate—obtained from a first synthesis of dimethyl carbonate or a recycling step—is subjected to a first fractionated distillation step for separation of methanol and an azeotropic mixture of dimethyl carbonate and methanol. Advantageously, the azeotropic mixture comprises a proportion by mass of dimethyl carbonate of approximately 30% in methanol.

Advantageously and according to the invention, a second fractionated distillation step is carried out in which at least a portion of the azeotropic mixture is brought into contact with at least one inorganic salt, and the mixture that is formed is heated in such a way as to form—by distillation/condensation at atmospheric pressure—a condensate that is enriched with dimethyl carbonate and that comprises at least 35% by mass of dimethyl carbonate. In this variant of a method according to the invention, the azeotropic mixture is enriched by distillation/condensation of said azeotropic mixture placed in contact with at least one inorganic salt selected from the group that is formed by zinc chloride (Zn) II ($ZnCl_2$), tin chlorides (Sn)—in particular tin chloride (Sn) II ($SnCl_2$)—and iron chloride (Fe) III ($FeCl_3$). In such a step for enriching the azeotropic mixture in the presence of at least one such inorganic salt, at least a portion of the methanol of the azeotropic mixture is trapped in the distillation medium, and the condensate that is enriched with dimethyl carbonate is formed.

In this variant of a method according to the invention, the second step for fractionated distillation of the azeotropic mixture is carried out in the absence of urea.

Advantageously, in another variant of a method according to the invention, the enriched condensate is subjected to a distillation at atmospheric pressure adapted to be able to form a condensate formed by an azeotropic mixture of dimethyl carbonate and methanol and a raffinate formed by dimethyl carbonate. Advantageously, the raffinate is formed by essentially pure dimethyl carbonate. In this variant of a method according to the invention, the raffinate formed by essentially pure dimethyl carbonate is recovered in the distillation reactor.

The invention further extends to all of the uses at atmospheric pressure of a saline ureic medium in the at least partially liquid state at a temperature of higher than 140° C. and comprising urea and at least one inorganic salt selected from the group formed by zinc chloride (Zn) II, tin chlorides (Sn), and iron chloride (Fe) III—in particular $SnCl_2$, $FeCl_3$, and $ZnCl_2$ at different hydration levels.

The invention extends in particular to all of the uses of such a saline ureic medium in organic synthesis, i.e., in a synthesis method and in particular in a method for synthesis and production of dimethyl carbonate.

The invention also relates to a method for synthesis of dimethyl carbonate at atmospheric pressure, a saline ureic medium, and the use of such a saline ureic medium, characterized in combination by all or part of the characteristics mentioned above or below.

Other objects, characteristics and advantages of the invention will emerge from reading the following description of different embodiments of a method according to the invention, examples provided solely in a nonlimiting manner and with the single FIGURE illustrating the steps of a particular variant of a method according to the invention.

In a method for synthesis of dimethyl carbonate according to the invention, a device 1 (experimental or industrial) for synthesis at atmospheric pressure comprising a double-jacketed reactor coupled to a distillation column making possible the operation of the experimental device with an infinite reflux level is used. The distillation column comprises a condenser and is equipped at the base of said condenser with a reflux control element making it possible, in a first closed position of the reflux control element, to guide the condensate toward the synthesis reactor via the distillation column (infinite reflux level) and, in a second open position of the reflux control element, to guide the condensate toward a collecting container separate from the synthesis reactor in which the condensate comprising the dimethyl carbonate is collected continuously.

The synthesis reactor is also equipped with an element for pumping and for introducing liquid methanol into the double-jacketed heating reactor, preferably configured to make it possible to introduce the liquid methanol drop by drop through the top of the reactor and so as to be able to bring into contact the liquid methanol and the liquid/solid reaction medium as soon as methanol is introduced. The experimental device is equipped with an element for mechanical stirring of the contents of the double-jacketed reactor.

In a first embodiment of a method for synthesis of dimethyl carbonate according to the invention, a quantity of at least one solid inorganic salt—in particular a chloride of a metal element—and optionally urea are placed in a synthesis reactor of a distillation device at atmospheric pressure comprising a distillation column topping the synthesis reactor, in such a way as to form an at least partially liquid saline ureic medium by heating at a temperature of between 80° C. and 125° C. for 10 minutes to 90 minutes. Such a saline ureic medium is a medium that is conductive and that also has the property of retaining methanol, in particular liquid methanol. In particular, each metal salt is selected from the group formed by zinc chloride ($ZnCl_2$), tin chloride ($SnCl_2$), and iron chloride ($FeCl_3$). More particularly, the tin chloride ($SnCl_2$) that, while having methanol-retaining properties, does not retain the ammonia formed during the formation of dimethyl carbonate and that can therefore be trapped in a water trap is selected.

The ratio of the molar quantity of inorganic salts to the molar quantity of urea is in general between 1 and 10, in particular approximately 3.

A quantity of solid catalyst, for example formed by zinc oxide and zinc sulfate in essentially equal proportions by mass and calcined in advance at a temperature of between 300° C. and 700° C. and stored protected from humidity, is then added into the synthesis reactor. The ratio of the molar quantity of urea to the molar quantity of solid catalyst is in general between 10 and 100, in particular approximately 50.

In this step, it is possible to add a quantity of liquid methanol into the synthesis reactor at atmospheric pressure before bringing the temperature in the synthesis reactor to a synthesis temperature of higher than 140° C.—in particular between approximately 140° C. and approximately 160° C. The synthesis temperature in the synthesis reactor is adapted in such a way as to keep the saline ureic medium, containing, if necessary, methanol, in an infinite reflux regime for about 15 minutes.

The temperature in the synthesis reactor is maintained in such a way as to form reaction vapors, and an addition of liquid methanol is initiated by simultaneously sampling with this addition a condensate formed by condensation of reaction vapors produced in the synthesis reactor and comprising dimethyl carbonate. From that time on, the distillation device at atmospheric pressure no longer operates at an infinite reflux level. The condensate formed by evaporation/condensation of the reaction medium consists of liquid methanol and dimethyl carbonate in a proportion by mass of approximately 5% dimethyl carbonate.

Thus, at least a portion of the dimethyl carbonate formed upon contact of the saline ureic medium is extracted from the saline ureic medium, and the equilibrium of the reaction is shifted toward the formation of said dimethyl carbonate. In addition, during the reaction of the methanol and the urea in the presence of inorganic salt(s) and catalyst, release of ammonia in gaseous form occurs, which ammonia is eliminated, at least partially, from the reaction medium. The inventors observed that, in an unpredictable and surprising way, said inorganic salt(s) of the liquid/solid medium, optionally in combination with urea and/or catalyst(s), make it possible at the same time to keep in the saline ureic medium a quantity of methanol in the liquid state for its reaction with urea and not to keep in the saline ureic medium the ammonia that is released during said reaction.

It is possible to add the quantity of liquid methanol in a continuous stream into the synthesis reactor. Of course, it is possible to carry out such an addition in a continuous stream by using a pump for introducing liquid methanol whose flow rate is controlled. The flow rate for introduction of liquid methanol into the saline ureic medium can be between 10 ml/h and 150 ml/h according to the initial quantities of inorganic salt(s), urea, and solid catalyst. However, nothing prevents liquid methanol from being added intermittently by successive inputs of discreet volumes of said liquid methanol into the saline ureic medium.

The total volume of added liquid methanol can vary according to the operating conditions. Quite obviously, the addition in the synthesis reactor of a large volume of liquid methanol can make it possible to obtain a high conversion level of urea into dimethyl carbonate. However, under such conditions, the value of the initial conversion level of urea into dimethyl carbonate (%) related to the initial urea concentration (mol/l) and the concentration of added liquid methanol will be minimized.

The reaction for synthesis of dimethyl carbonate is interrupted by interrupting the introduction of liquid methanol into the reaction medium while keeping the heating of the reactor at the synthesis temperature for about 15 minutes after the introduction of the liquid methanol is stopped and while collecting the condensate. Then, the heating is interrupted, and the synthesis reactor and the reaction medium are left to cool until the ambient temperature is reached.

In a second embodiment of a method for synthesis of dimethyl carbonate according to the invention, a saline ureic medium is prepared in the synthesis reactor by mixing at least one inorganic salt, urea and a solid catalyst, and, if necessary, liquid methanol. The reactor is heated at atmospheric pressure and at a temperature of between approximately 140° C. and approximately 160° C. in such a way as to form the saline ureic medium and by keeping it at an infinite reflux level for a duration of about 15 minutes. As soon as the saline ureic medium has an infinite reflux, liquid methanol is added, and the condensate formed by methanol and dimethyl carbonate are collected.

In a third embodiment of a synthesis method according to the invention, the condensate formed by methanol and dimethyl carbonate is collected, and said condensate is subjected to a subsequent step for enriching the dimethyl carbonate condensate by fractionated distillation during which a first fraction, formed by methanol and able to be recycled in a subsequent step for synthesizing dimethyl carbonate, is collected, and then a second fraction, a so-called azeotropic mixture, formed by methanol and dimethyl carbonate, is collected. In this third embodiment, a mixture that is close to the azeotrope and enriched with dimethyl carbonate in relation to the condensate and comprising up to 30% (by mass) of dimethyl carbonate and at least 70% by mass of methanol is therefore formed. In this third embodiment, the first methanol-rich fraction is collected, and said first methanol-rich fraction is recycled in a method for synthesizing dimethyl carbonate at atmospheric pressure according to one of the first three embodiments of a method according to the invention. It is also possible to reuse the first methanol-rich fraction in any method in which methanol can be used.

In a fourth embodiment of a synthesis method according to the invention, the azeotropic mixture is collected, and it is subjected to a second subsequent step of fractionated distillation in which the azeotropic mixture is placed in contact with inorganic salt(s) in the synthesis reactor of a device for distillation at atmospheric pressure comprising a distillation column topping the synthesis reactor; the azeotropic mixture is heated upon contact with inorganic salt(s) in such a way as to trap at least one portion of the methanol of the azeotropic mixture in the synthesis reactor and to form, by distillation/condensation at atmospheric pressure, a composition of dimethyl carbonate comprising approximately 35% by mass of dimethyl carbonate.

In this fourth embodiment of a synthesis method according to the invention, a composition that comprises methanol, inorganic salts, and optionally dimethyl carbonate is therefore formed in the synthesis reactor. The inorganic salts are likely to be able to be precipitated for a subsequent reuse in the reactor for synthesis of a method according to one of the first three embodiments or a subsequent step of azeotropic resolution according to the fourth embodiment.

In a fifth embodiment of a synthesis method according to the invention, the dimethyl carbonate composition, comprising approximately 35% by mass of dimethyl carbonate, is subjected to a distillation step that is fractionated at atmospheric pressure that is suitable for being able to form a condensate formed by an azeotropic mixture of dimethyl carbonate and methanol and a raffinate formed by essentially pure dimethyl carbonate.

A method in which the first or the second embodiment is combined with the third, fourth and fifth embodiments is shown in FIG. 1. In a first synthesis step 1 of the method shown, reaction vapors are formed in the synthesis reactor 10 by heating methanol, a saline ureic medium, and a catalyst. These vapors are condensed in a distillation column 111, and a distillate is collected at the top 12 of the distillation column. The distillate comprises a proportion of approximately 5% dimethyl carbonate and methanol.

In a second step 2 for enriching the distillate with dimethyl carbonate, the distillate formed in the first step 1 is placed in a distillation reactor 20, and it is heated in such a way as to sample by distillation at the top of a distillation column 112 an azeotropic composition 13 comprising approximately 30% dimethyl carbonate and to preserve in the reactor 20 excess methanol that is likely to be advantageously reused for a subsequent synthesis step 1.

In a third separation step 3, the azeotropic composition 13 is placed in a reactor 30 for heating in the presence of a quantity of salt from a saline ureic medium, and the reactor 30 is heated so as to form at the top of a distillation column 113 a composition 14 that is enriched with dimethyl carbonate and that comprises, for example, approximately 35% dimethyl carbonate and methanol. A mixture that comprises methanol, dimethyl carbonate, and salt from the saline ureic medium is also recovered in the reactor 30. This mixture is likely to be able to be advantageously reused in a reactor 10 for synthesis of a subsequent synthesis step 1.

In a fourth step 4 for purifying dimethyl carbonate, the enriched composition 14 is subjected to a distillation in a distillation reactor 40 and in which an azeotropic composition 15 is formed at the top of a distillation column 114, said composition comprising approximately 30% dimethyl carbonate and essentially pure dimethyl carbonate 16 in the distillation reactor 40. In a method according to the invention, the azeotropic composition 15 is advantageously recycled in the heating reactor 30 in such a way as to form a subsequent enriched composition 14.

EXAMPLE 1

Preparation of the Zinc Oxide/Zinc Sulfate Catalyst

In a container, equivalent masses of zinc oxide and zinc sulfate are mixed. After grinding, it is diluted in dichloromethane for homogenizing the mixture. After evaporation of the solvent, the preparation is calcined for 4 hours at 500° C. The catalyst is then stored protected from humidity in a hermetically-sealed container.

EXAMPLE 2

Synthesis of Dimethyl Carbonate from Urea, Methanol, Tin Chloride ($SnCl_2$) and Zinc Oxide/Zinc Sulfate ($ZnO/ZnSO_4$) as Catalyst 75 g of $SnCl_2$ and 8 g of urea are introduced into a 250-ml double-jacketed reactor equipped with a distillation column and a stirring device. The mixture that is obtained by carrying the fluid circulating in the double jacket is heated while being stirred at the temperature of 100° C. for 20 minutes in such a way as to form a saline ureic medium. Then, 0.4 g of catalyst $ZnO/ZnSO_4$, as obtained in Example 1, is added into the saline ureic medium that is obtained. Then, 15 ml of methanol is added, and the temperature of the double jacket is brought to 165° C. in such a way as to reach the synthesis temperature in the reactor (taking into account the addition of cold methanol, and the evaporation of volatile components) by maintaining infinite reflux conditions for 15 minutes. No condensate is therefore sampled in this step. Liquid methanol is then introduced into the reactor at a rate of 120 ml of methanol per hour (120 ml/h) for 4 hours (or a total of 480 ml of methanol). During this phase, a condensate is continuously sampled at the top of the distillation column. After 4 hours of reaction, the introduction of methanol is interrupted, and then, after 15 minutes, the heating of the reactor is interrupted.

Analysis by gas phase chromatography of the condensate makes it possible to determine that the rate of conversion of the urea into dimethyl carbonate is 33%. The concentration of the dimethyl carbonate in the distillate is 11.4 mg of dimethyl carbonate per gram of condensate.

EXAMPLE 3

Synthesis of Dimethyl Carbonate from Urea, Methanol, Zinc Chloride ($ZnCl_2$) and Zinc Oxide/Zinc Sulfate ($ZnO/ZnSO_4$) as Catalyst 75 g of $ZnCl_2$ and 8 g of urea are introduced into a 250-ml, double-jacketed reactor equipped with a distillation column and a stirring device. The mixture that is obtained is heated while being stirred by bringing the fluid circulating in the double jacket to the temperature of 100° C. for 20 minutes in such a way as to form a liquid saline ureic medium. 0.4 g of catalyst $ZnO/ZnSO_4$, as obtained in Example 1, is then added into the saline ureic medium that is obtained. Then, 35 ml of methanol is added, and the temperature of the double jacket is brought to 165° C. in such a way as to reach the synthesis temperature in the reactor by maintaining infinite reflux conditions for 15 minutes. No condensate is therefore sampled in this step. Then, liquid methanol is introduced into the reactor at a rate of 115 ml of methanol per hour (115 ml/h) for 4 hours (or a total of 480 ml of methanol). During this phase, a condensate is continuously sampled at the top of the distillation column. After 4 hours of reaction, the introduction of the methanol is interrupted, and then, after 15 minutes, the heating of the reactor is interrupted.

Analysis by gas phase chromatography of the condensate makes it possible to determine that the rate of conversion of the urea into dimethyl carbonate is 23%. The concentration of dimethyl carbonate in the distillate is 8.5 mg of dimethyl carbonate per gram of condensate.

EXAMPLE 4

Synthesis of Dimethyl Carbonate Starting from Urea, Methanol, Zinc Chloride ($ZnCl_2$) and Zinc Oxide/Zinc Sulfate ($ZnO/ZnSO_4$) as Catalyst 75 g of $ZnCl_2$, 8 g of urea, and 0.4 g of catalyst $ZnO/ZnSO_4$, as obtained in Example 1, are introduced into a 250-ml double-jacketed reactor equipped with a distillation column and a stirring device. 15 ml of methanol is added, and the temperature of the fluid circulating in the double jacket is brought to the temperature of 165° C. in such a way as to reach the synthesis temperature in the reactor by maintaining infinite reflux conditions for 15 minutes. Then, liquid methanol is introduced into the reactor in a continuous stream at a rate of 120 ml of methanol per hour (120 ml/h) for 4 hours (or a total of 480 ml of methanol). During this phase of adding methanol, a condensate is sampled continuously at the top of the distillation column. After 4 hours of reaction, the introduction of the methanol is interrupted, and then, after 15 minutes, the heating of the reactor is interrupted.

Analysis by gas phase chromatography of the condensate makes it possible to determine that the rate of conversion of the urea into dimethyl carbonate is 29%. The concentration of dimethyl carbonate in the distillate is 10.2 mg of dimethyl carbonate per gram of condensate.

EXAMPLE 5

Synthesis of Dimethyl Carbonate from Urea, Methanol, Zinc Oxide and Zinc Sulfate as Catalyst and Zinc Chloride as Inorganic Salt 20 g of $ZnCl_2$ and 5 g of urea are introduced into a 250-ml flask equipped with a distillation column topped by a Dean-Stark device, and then the mixture that is obtained is heated in an oil bath at the temperature of 100° C. for 2 hours at atmospheric pressure. Then, 0.1 g of catalyst $ZnO/ZnSO_4$, as described in Example 1, is added. Then, 5 g of methanol is added, and the temperature of the oil bath is brought to 165° C. in such a way as to reach the synthesis temperature in the flask, and this temperature is maintained for 15 minutes. Still at synthesis temperature, an addition of methanol at a rate of 5 g of methanol per hour for 4 hours is carried out by sampling the condensate continuously. After 4 hours of reaction, the introduction of the methanol is interrupted, and then, after an additional 15 minutes, the flask is removed from the oil bath.

The rate of conversion of the urea into dimethyl carbonate is 16%.

EXAMPLE 6

Synthesis of Dimethyl Carbonate from Urea, Methanol, $ZnO/ZnSO_4$ as Catalyst and $SnCl_2$ as Inorganic Salt The procedure is performed identically to Example 5 but by replacing $ZnCl_2$ by $SnCl_2$. The rate of conversion of the urea into dimethyl carbonate is 33%.

EXAMPLE 7

Synthesis of Dimethyl Carbonate from Urea, Methanol, $ZnO/ZnSO_4$ as Catalyst and $FeCl_3$ as Inorganic Salt The procedure is performed identically to Example 5 but by replacing $ZnCl_2$ by $FeCl_3$. The rate of conversion of the urea into dimethyl carbonate is 30%.

EXAMPLE 8

Synthesis of Dimethyl Carbonate from Urea, Methanol, $ZnO/ZnSO_4$ as Catalyst and an $SnCl_2/ZnCl_2$ Mixture 10 g of $ZnCl_2$, 10 g of $SnCl_2$, and 5 g of urea are introduced into a 250-ml flask as described in Example 6, and then the mixture that is obtained is heated in an oil bath at 100° C. for a duration of about 2 hours at atmospheric pressure. Then, 0.1 g of catalyst is added as described in Example 1. Then, 5 g of methanol is added into the flask, the temperature of the oil bath is brought to 165° C. so as to reach the synthesis temperature in the flask, and this temperature is maintained for 15 minutes. Still at the synthesis temperature, an addition of methanol is carried out at a rate of 5 g of methanol per hour for 4 hours by sampling the condensate continuously. After 4 hours of reaction, the introduction of methanol is interrupted, and then, after 15 additional minutes, the flask is removed from the oil bath.

The rate of conversion of the urea into dimethyl carbonate is 22%.

EXAMPLE 9

Synthesis of Dimethyl Carbonate from Urea, Methanol, Tin Chloride ($SnCl_2$) and Zinc Oxide/Zinc Sulfate ($ZnO/ZnSO_4$) as Catalyst 150 g of $SnCl_2$, 16 g of urea, and 0.8 g of catalyst $ZnO/ZnSO_4$, as obtained in Example 1, are introduced into a 250-ml double-jacketed reactor equipped with a distillation column and a stirring device. 25 ml of methanol is added, and the temperature of the fluid circulating in the double jacket is brought to the temperature of 165° C. in such a way as to reach the synthesis temperature in the reactor by maintaining infinite reflux conditions for 15 minutes.

Then, a reflux rate of 75 (reflux/distillate) is imposed, and liquid methanol is introduced into the reactor in a continuous stream at a rate of 33.75 ml of methanol per hour (33.75 ml/h) for 4 hours (or a total of 135 ml of methanol). During this phase of adding methanol, a condensate is sampled continuously at the top of the distillation column. After 4 hours of reaction, the introduction of the methanol is interrupted, and then, after 15 minutes, the heating of the reactor is interrupted.

Analysis by gas phase chromatography of the condensate makes it possible to determine that the rate of conversion of the urea into dimethyl carbonate is 19%. The concentration of the dimethyl carbonate in the distillate is 51.2 mg of dimethyl carbonate per gram of condensate.

EXAMPLE 10

Synthesis of Dimethyl Carbonate from Urea, Methanol, Tin Chloride ($SnCl_2$) and Zinc Oxide/Zinc Sulfate ($ZnO/ZnSO_4$) as Catalyst 150 g of $SnCl_2$, 16 g of urea, and 0.8 g of catalyst $ZnO/ZnSO_4$, as obtained in Example 1, are introduced into a 250-ml double-jacketed reactor equipped with a distillation column and a stirring device. 25 ml of methanol is added, and the temperature of the fluid circulating in the double jacket is brought to the temperature of 165° C. in such a way as to reach the synthesis temperature in the reactor by maintaining infinite reflux conditions for 15 minutes. A reflux rate of 75 (reflux/distillate) is then imposed, and liquid methanol is introduced into the reactor in a continuous stream at a rate of 30 ml of methanol per hour (30 ml/h) for 10.5 hours (or a total of 315 ml of methanol). During the reaction, the reflux rate is reduced to the value of 20 so that the temperature in the reactor exceeds 140° C. After 10.5 hours of reaction, the introduction of methanol is interrupted, and then, after 15 minutes, the heating of the reactor is interrupted.

Analysis by gas phase chromatography of the distillate makes it possible to determine that the rate of conversion of the urea into dimethyl carbonate is 38.8%. The concentration of dimethyl carbonate in the distillate is 52.3 mg of dimethyl carbonate per gram of condensate.

EXAMPLE 11

Enrichment of Dimethyl Carbonate of a Mixture that Consists of 29% (by Mass) of Dimethyl Carbonate and 71% (by Mass) of Methanol 20 g of a mixture that consists of 29% (by mass) of dimethyl carbonate and 71% (by mass) of methanol are introduced into a flask topped by a distillation column. 10 g of zinc chloride is added. The flask is heated in such a way as to form a distillate by complete distillation of the mixture. The temperature of the distiller at the end of distillation reaches approximately 173° C.

14.9 g of a distillate comprising 35.2% by mass of dimethyl carbonate corresponding to a recovery yield of 90.4% of the initial dimethyl carbonate is thus collected.

EXAMPLE 12

Enrichment of Dimethyl Carbonate of a Mixture Consisting of 29% (by Mass) of Dimethyl Carbonate and 71% (by Mass) of Methanol 20 g of a mixture that consists of 29% (by mass) of dimethyl carbonate and 71% (by mass) of methanol are introduced into a flask topped by a distillation column. 10 g of tin chloride is added. The flask is heated so as to collect a distillate until the temperature in the distiller reaches approximately 80° C.

9.3 g of a distillate comprising 34% by mass of dimethyl carbonate corresponding to a recovery yield of 54.5% of the initial dimethyl carbonate is thus collected.

EXAMPLE 13

Purification of Dimethyl Carbonate of a Mixture that Consists of 40% (by Mass) of Dimethyl Carbonate and 60% (by Mass) of Methanol 1 kg of a mixture that consists of 40% (by mass) of dimethyl carbonate and 60% (by mass) of methanol are introduced into a distiller with a 2-liter capacity topped by a 30-plate distillation column. The distiller is heated in such a way as to collect a distillate that comprises 35% to 38% of dimethyl carbonate. At the end of the distillation, the temperature in the distiller is 93° C. 112.65 g of dimethyl carbonate having a purity of 99.8% and representing 28% of the initial dimethyl carbonate are recovered in the distiller.

The invention can have numerous modifications and variants such as, for example, the selection of the device for synthesis and for heating and the separating performance levels of the distillation column.

The invention claimed is:

1. Method for synthesizing dimethyl carbonate starting from methanol and urea, in which a saline ureic medium comprising at least one inorganic salt selected from the group consisting essentially of zinc chloride (Zn) II, tin chlorides (Sn), and iron chloride (Fe) III is used:

wherein:

methanol, in the presence of a catalytic composition, is brought into contact with said saline ureic medium that is at least partially liquid at a temperature, so-called synthesis temperature, that is higher than 140° C., such that reaction vapors are produced;

the reaction vapors are condensed, and a condensate of said reaction vapors and that comprises dimethyl carbonate is recovered;

the method is implemented at atmospheric pressure.

2. Method according to claim 1, wherein during a first operating step, a reaction medium that comprises the saline ureic medium, the catalytic composition, and a first quantity of methanol is formed, and the reaction medium is kept at the synthesis temperature, with the formed condensate being reintroduced into the reaction medium, and then during a second subsequent operating step, a stream of methanol is introduced into the reaction medium, and a stream of the condensate of the reaction vapors is sampled.

3. Method according to claim 2, wherein the first step is of a duration of about 15 minutes.

4. Method according to claim 2, wherein methanol is added in a continuous stream into the reaction medium.

5. Method according to claim 2, wherein methanol is added in an intermittent stream into the reaction medium.

6. Method according to claim 1, wherein the saline ureic medium is formed initially by heating a saline composition comprising each inorganic salt and urea.

7. Method according to claim 6, wherein the saline composition is heated at a temperature of between 80° C. and 125° C. and for a duration of at least 10 minutes.

8. Method according to claim 1, wherein the saline ureic medium is prepared with an initial quantity of urea and an initial quantity of each inorganic salt in a ratio by mass of each inorganic salt in relation to the urea of between 2 and 10.

9. Method according to claim 1, wherein the saline ureic medium is a conductive medium.

10. Method according to claim 1, wherein the catalytic composition comprises at least one compound that is selected from the group formed by zinc oxide and zinc sulfate.

11. Method according to claim 1, wherein the catalytic composition is prepared by calcination of a solid mixture comprising zinc oxide and zinc sulfate at a temperature of between 300° C. and 700° C.

12. Method according to claim 1, wherein methanol is added in the liquid state into the reaction medium.

13. Method according to claim 1, wherein a stream of at least one portion of the condensate of reaction vapors is introduced into a reaction medium kept at the synthesis temperature and comprising a quantity of saline ureic medium and a quantity of catalytic composition, such that reaction vapors are produced, and said reaction vapors are condensed, and a condensate of said reaction vapors comprising dimethyl carbonate is recovered.

14. Method according to claim 1, wherein at least a portion of the condensate is subjected to a first step for fractionated distillation and for separation of methanol and an azeotropic mixture of dimethyl carbonate and methanol.

15. Method according to claim 14, wherein a second fractionated distillation step is carried out in which at least a portion of the azeotropic mixture is brought into contact with at least one inorganic salt, and the mixture that is formed is heated in such a way as to form—by distillation/condensation at atmospheric pressure—a condensate that is enriched with dimethyl carbonate and that comprises at least 35% by mass of dimethyl carbonate.

16. Method according to claim 15, wherein the enriched condensate is subjected to a distillation at atmospheric pressure that is suitable for being able to form a condensate that is formed by an azeotropic mixture of dimethyl carbonate and methanol and a raffinate formed by dimethyl carbonate.

17. Method according to claim 3, wherein methanol is added in a continuous stream into the reaction medium.

18. Method according to claim 3, wherein methanol is added in an intermittent stream into the reaction medium.

19. A saline ureic medium in the at least partially liquid state at a temperature of higher than 140° C. for use in organic synthesis comprising urea and at least one inorganic salt that is selected from the group consisting essentially of zinc chloride (Zn) II, tin chlorides (Sn), and iron chloride (Fe) III.

* * * * *